United States Patent
Aoyama et al.

(10) Patent No.: US 12,145,300 B2
(45) Date of Patent: Nov. 19, 2024

(54) METHOD FOR TESTING MELT-PROCESSIBLE FLUORORESIN INJECTION-MOLDED PRODUCT AND METHOD FOR PRODUCING MELT-PROCESSIBLE FLUORORESIN INJECTION-MOLDED PRODUCT

(71) Applicant: DAIKIN INDUSTRIES, LTD., Osaka (JP)

(72) Inventors: Takahisa Aoyama, Osaka (JP); Hayato Tsuda, Osaka (JP); Yuuki Kuwajima, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 761 days.

(21) Appl. No.: 17/259,840

(22) PCT Filed: Jun. 17, 2019

(86) PCT No.: PCT/JP2019/023907
§ 371 (c)(1),
(2) Date: Jan. 12, 2021

(87) PCT Pub. No.: WO2020/017215
PCT Pub. Date: Jan. 23, 2020

(65) Prior Publication Data
US 2023/0066133 A1    Mar. 2, 2023

(30) Foreign Application Priority Data
Jul. 17, 2018  (JP) ................. 2018-134253

(51) Int. Cl.
*G01N 3/08* (2006.01)
*B29C 45/76* (2006.01)
*G01N 33/44* (2006.01)

(52) U.S. Cl.
CPC ........... *B29C 45/7686* (2013.01); *G01N 3/08* (2013.01); *G01N 33/442* (2013.01); *G01N 2203/0017* (2013.01); *G01N 2203/0075* (2013.01)

(58) Field of Classification Search
CPC .. B29C 45/7686; B29C 45/17; G01N 33/442; G01N 2203/0017; G01N 2203/0075; G01N 3/08
See application file for complete search history.

(56) References Cited

U.S. PATENT DOCUMENTS

| | | | | |
|---|---|---|---|---|
| 2014/0287177 A1* | 9/2014 | Suda | ....................... | C08F 14/26 525/200 |
| 2023/0272136 A1* | 8/2023 | Zenke | ....................... | C08F 8/00 526/247 |
| 2023/0295356 A1* | 9/2023 | Isaka | ....................... | H01B 3/445 428/375 |

FOREIGN PATENT DOCUMENTS

| | | | |
|---|---|---|---|
| JP | 2014228290 A | * | 12/2014 |
| JP | 2017-030371 A | | 2/2017 |

OTHER PUBLICATIONS

Extended European Search Report issued Nov. 11, 2021 in counterpart European Application No. 19838426.5.

(Continued)

*Primary Examiner* — Jennifer Bahls
(74) *Attorney, Agent, or Firm* — Sughrue Mion, PLLC

(57) ABSTRACT

Provided is a method for testing a melt-fabricable fluororesin injection-molded article which enables easy determination of whether or not a tested article is a defective article due to a crack or delamination. The method for testing a melt-fabricable fluororesin injection-molded article includes determining whether or not a melt-fabricable fluororesin injection-molded article is defective due to a crack or delamination based on a stress-strain curve or tensile (Continued)

strength-strain curve obtained by a tensile test performed on the injection-molded article.

7 Claims, 4 Drawing Sheets

(56) References Cited

OTHER PUBLICATIONS

English Translation of International Preliminary Report on Patentability with translation of Written Opinion dated Jan. 19, 2021, in Application No. PCT/JP2019/023907.
International Search Report for PCT/JP2019/023907 dated Sep. 17, 2019 [PCT/ISA/210].

* cited by examiner

METHOD FOR TESTING MELT-PROCESSIBLE FLUORORESIN INJECTION-MOLDED PRODUCT AND METHOD FOR PRODUCING MELT-PROCESSIBLE FLUORORESIN INJECTION-MOLDED PRODUCT

CROSS-REFERENCE TO RELATED APPLICATIONS

This application is a National Stage of International Application No. PCT/JP2019/023907 filed Jun. 17, 2019, claiming priority based on Japanese Patent Application No. 2018-134253 filed Jul. 17, 2018.

TECHNICAL FIELD

The disclosure relates to methods for testing a melt-fabricable fluororesin injection-molded article and methods for producing a melt-fabricable fluororesin injection-molded article.

BACKGROUND ART

Fluororesin having excellent properties including heat resistance, abrasion resistance, and chemical resistance is widely used as a typical type of engineering plastics. An exemplary molding method of fluororesin is injection molding.

Patent Literature 1, for example, discloses a method for producing an injection-molded article having a projected area in the injection direction of 1100 cm² or more, the method including injection-molding a composition containing a hot-melt fluororesin that is a tetrafluoroethylene/fluoroalkoxytrifluoroethylene copolymer and polytetrafluoroethylene at an injection pressure of 400 kg/cm² or more but 800 kg/cm² or less.

CITATION LIST

Patent Literature

Patent Literature 1: JP 2017-30371 A

SUMMARY OF INVENTION

Technical Problem

The disclosure aims to provide a method for testing a melt-fabricable fluororesin injection-molded article which enables easy determination of whether or not a tested article is a defective article due to a crack or delamination.

Solution To Problem

The disclosure provides a method for testing a melt-fabricable fluororesin injection-molded article, the method including determining whether or not a melt-fabricable fluororesin injection-molded article is defective due to a crack or delamination based on a stress-strain curve or tensile strength-strain curve obtained by a tensile test performed on the injection-molded article.

The determining step preferably involves dividing the stress-strain curve or tensile strength-strain curve into two or more regions according to a strain level, obtaining a reduction amount or reduction rate of the stress or tensile strength in a large strain region relative to the stress or tensile strength in a small strain region, and determining an injection-molded article having a small reduction amount or reduction rate of the stress or tensile strength as a non-defective article and an injection-molded article having a large reduction amount or reduction rate of the stress or tensile strength as a defective article.

The determining step preferably involves obtaining a reduction amount or reduction rate of a minimum stress or minimum tensile strength in a region of the strain of $Z^1$% to $Z^2$% where $Z^1$ represents a value of $Y^1$ defined below to 200 and $Z^2$ represents a value of larger than $Z^1$ but not larger than 300 relative to a maximum stress or maximum tensile strength in a region of the strain of $Y^1$% or lower where $Y^1$ represents a value of 5 to 80 in the stress-strain curve or tensile strength-strain curve, and determining an injection-molded article having a small reduction amount or reduction rate of the stress or tensile strength as a non-defective article and an injection-molded article having a large reduction amount or reduction rate of the stress or tensile strength as a defective article.

The determining step preferably involves obtaining a reduction amount or reduction rate of the stress or tensile strength in a region of the strain of $Z^3$% where $Z^3$ represents a value of $Y^2$ defined below to 300 relative to a maximum stress or maximum tensile strength in a region of the strain of $Y^2$% or lower where $Y^2$ represents a value of 5 to 80 in the stress-strain curve or tensile strength-strain curve, and determining an injection-molded article having a small reduction amount or reduction rate of the stress or tensile strength as a non-defective article and an injection-molded article having a large reduction amount or reduction rate of the stress or tensile strength as a defective article.

The determining step preferably involves dividing the stress-strain curve into n regions for every X % of the strain where X represents a value of 5 or larger, calculating a maximum value $SMAX_m$ and a minimum value $SMIN_m$ of the stress in each region, and determining an injection-molded article having $SMAX_m$ and $SMIN_{m+1}$ satisfying the following expression (1) as a non-defective article and an injection-molded article having $SMAX_m$ and $SMIN_{m+1}$ not satisfying the expression (1) as a defective article:

$$SMAX_m \times \alpha \leq SMIN_{m+1} \tag{1}$$

where α represents a value of 0.90 or larger and m represents an integer of 1 to (n−1).

The determining step also preferably involves dividing the tensile strength-strain curve into n regions for every X % of the strain where X represents a value of 5 or larger, calculating a maximum value $TMAX_m$ and a minimum value $TMIN_m$ of the tensile strength in each region, and determining an injection-molded article having $TMAX_m$ and $TMIN_{m+1}$ satisfying the following expression (2) as a non-defective article and an injection-molded article having $TMAX_m$ and $TMIN_{m+1}$ not satisfying the expression (2) as a defective article:

$$TMAX_m \times \alpha \leq TMIN_{m+1} \tag{2}$$

where α represents a value of 0.90 or larger and m represents an integer of 1 to (n−1).

The melt-fabricable fluororesin injection-molded article includes a fluororesin including at least one selected from the group consisting of a tetrafluoroethylene/perfluoro(alkyl vinyl ether) copolymer and a tetrafluoroethylene/hexafluoropropylene copolymer.

The disclosure also provides a method for producing a melt-fabricable fluororesin injection-molded article, the method including: (x) injection-molding a melt-fabricable fluororesin of a lot to obtain multiple injection-molded articles; (y) randomly selecting at least one injection-molded article from the multiple injection-molded articles and determining whether or not the selected injection-molded article is defective due to a crack or delamination based on a stress-strain curve or tensile strength-strain curve obtained by a tensile test; and (z) sorting out a non-defective article in the injection-molded articles produced from the melt-fabricable fluororesin of the same lot from which the injection-molded article determined as a defective article has been produced.

Advantageous Effects of Invention

The production method of the disclosure having the above configuration enables easy determination of whether or not a melt-fabricable fluororesin injection-molded article is defective due to a crack or delamination.

DESCRIPTION OF EMBODIMENTS

Figure 1:
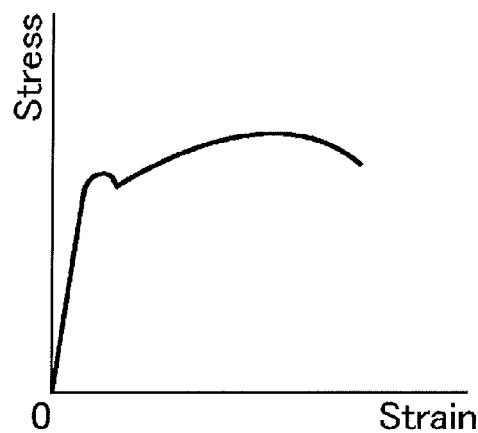
FIG. 1 is a schematic view showing an example of a stress-strain curve.

A melt-fabricable fluororesin is molded, for example, by compression molding or injection molding. In the case of injection molding, a resulting molded article may possibly suffer cracks or delamination. The cracks or delamination in an injection-molded article can be observed under a microscope. However, it requires preparation of, as a specimen, a film of a cross-sectional slice having a smooth and flawless surface and a uniform thickness of 20 to 100 micrometers. Such a specimen needs to be prepared using a special instrument such as a microtome with careful attention to the outcome, which takes a considerable effort. In addition, the presence of cracks needs to be confirmed by human eyes, which requires extra work. Moreover, since some slight cracks or delamination does not affect the quality of the injection-molded article, determination of whether or not an injection-molded article is defective is difficult.

The inventors made intensive studies to find out that quantitative analysis of a stress-strain curve or tensile strength-strain curve obtained by a tensile test allows determination of whether or not an article is defective due to cracks or delamination. Thus, the test method of the disclosure was developed.

Hereafter, the test method of the disclosure is specifically described.

The test method of the disclosure includes determining whether or not a melt-fabricable fluororesin injection-molded article is defective due to a crack or delamination based on a stress-strain curve or tensile strength-strain curve obtained by a tensile test performed on the injection-molded article.

The melt-fabricable fluororesin injection-molded article refers to a molded article obtained by injection molding of a melt-fabricable fluororesin.

The term "melt-fabricable" means that it is processible in a molten state with use of a conventional processor such as an injection molding apparatus. The melt-fabricable fluororesin typically has a melt flow rate (MFR) of 0.01 to 500 g/10 min.

MFR as used herein is a value obtained by measurement in accordance with ASTM D 1238 at a temperature of 372° C. and a load of 5 kg.

Examples of the melt-fabricable fluororesin include a tetrafluoroethylene [TFE]/perfluoro(alkyl vinyl ether) [PAVE] copolymer [PFA], a TFE/hexafluoropropylene [HFP] copolymer [FEP], an ethylene [Et]/TFE copolymer [ETFE], an Et/TFE/HFP copolymer, polychlorotrifluoroethylene [PCTFE], a chlorotrifluoroethylene [CTFE]/TFE copolymer, an Et/CTFE copolymer, polyvinylidene fluoride [PVDF], and polyvinyl fluoride [PVF]. From the standpoint of heat resistance, preferred is at least one selected from the group consisting of PFA, FEP, ETFE, an Et/TFE/HFP copolymer, PCTFE, a CTFE/TFE copolymer, an Et/CTFE copolymer, and PVDF, and more preferred is at least one selected from the group consisting of PFA and FEP.

Though not limited, the PFA is preferably a copolymer containing a TFE unit and a PAVE unit at a molar ratio (TFE unit/PAVE unit) of 70/30 or more but less than 99.5/0.5. The molar ratio is more preferably 70/30 to 98.9/1.1, still more preferably 80/20 to 98.5/1.5. A PFA containing too small an amount of the TFE unit tends to have lower mechanical properties, while a PFA containing too large an amount of the TFE unit tends to have too high a melting point, which lowers the moldability. The PFA may be a copolymer consisting only of TFE and PAVE or, preferably, a copolymer containing a monomer unit derived from a monomer copolymerizable with TFE and PAVE in an amount of 0.1 to 10 mol % and the TFE unit and the PAVE unit in a total amount of 90 to 99.9 mol %. Examples of the monomer copolymerizable with TFE and PAVE include HFP, a vinyl monomer represented by $CZ^3Z^4=CZ^5(CF_2)nZ^6$ (wherein $Z^3$, $Z^4$, and $Z^5$ are the same as or different from each other and each represent a hydrogen atom or a fluorine atom, $Z^6$ represents a hydrogen atom, a fluorine atom, or a chlorine atom, and n represents an integer of 2 to 10), and an alkyl perfluorovinyl ether derivative represented by $CF_2=CF-OCH_2-Rf^7$ (wherein $Rf^7$ represents a C1-C5 perfluoroalkyl group).

The PFA has a melting point of preferably 180° C. to 340° C., more preferably 230° C. to 330° C., still more preferably 280° C. to 320° C. The melting point is a temperature corresponding to the maximum value in a heat-of-fusion curve obtained by heating at a rate of 10° C./min using a differential scanning calorimeter (DSC).

The PFA has a melt flow rate (MFR) of preferably 0.1 to 100 g/10 min, more preferably 0.5 to 90 g/10 min, still more preferably 1.0 to 85 g/10 min.

Though not limited, the FEP is preferably a copolymer containing a TFE unit and a HFP unit at a molar ratio (TFE unit/HFP unit) of 70/30 or more but less than 99/1. The molar ratio is more preferably 70/30 to 98.9/1.1, still more preferably 80/20 to 97/3. A FEP containing too small an amount of the TFE unit tends to have lower mechanical properties, while a FEP containing too large an amount of the TFE unit tends to have too high a melting point, which lowers the moldability. The FEP is also preferably a copolymer containing a monomer unit derived from a monomer copolymerizable with TFE and HFP in an amount of 0.1 to 10 mol % and the TFE unit and the HFP unit in a total amount of 90 to 99.9 moil. Examples of the monomer copolymerizable with TFE and HFP include PAVE and an alkyl perfluorovinyl ether derivative.

The FEP has a melting point of preferably 150° C. to 320° C., more preferably 200° C. to 300° C., still more preferably 240° C. to 280° C. The melting point is a temperature corresponding to the maximum value in a melting heat curve obtained by heating at a rate of 10° C./min using a differential scanning calorimeter (DSC).

The FEP has a MFR of preferably 0.01 to 100 g/10 min, more preferably 0.1 to 80 g/10 min, still more preferably 1 to 60 g/10 min, particularly preferably 1 to 50 g/10 min.

The amount of each monomer unit constituting the fluororesin herein can be calculated by NMR, FT-IR, elemental analysis, and fluorescence X-ray analysis combined as appropriate in accordance with the type of the monomer.

The injection molding is not limited, and the test method of the disclosure is employable for injection-molded articles obtained by any injection molding. The test method of the disclosure may include a step of injection-molding a melt-fabricable fluororesin to obtain a melt-fabricable fluororesin injection-molded article.

The injection-molded article may have any shape. The test method of the disclosure is employable for an injection-molded article in any shape such as a sheet shape or a cylinder shape.

An injection-molded article may be subjected to a tensile test as it is. In some cases, part of an injection-molded article is preferably taken out to be used as a specimen for higher accuracy. Since a common injection-molded article has a non-uniform thickness and irregularities such as protrusions or holes, it may be difficult to perform a tensile test with high accuracy and reproducibility on such an injection-molded article as it is.

In the case where the injection-molded article is large enough to obtain a standard specimen, the standard specimen can be used as a specimen. In the case where the injection-molded article is not large enough to obtain a standard specimen, the shape of the specimen may be a strip, a miniature shape of the standard specimen, or the like.

In the case where the injection-molded article has a shape which is not a simple sheet, such as a shape having thickness non-uniformity, the thickness non-uniformity may be reduced at a part to be involved in a tensile test in advance by grinding, machining, or cutting.

In order to limit the part involved in a tensile test, two pairs of jigs made for clamping just outside of the part to be involved in a tensile test may be used in a tensile test. Adjustment of the clamping parts with the jigs can minimize the influence by portions having a non-uniform thickness, protrusions, holes, or the like.

Two pairs of jigs may be made in a manner that they engage with the protrusions on the injection-molded article. In a tensile test, protrusions are fit into the jigs, and therefore, an influence by slippage of the specimen at a chuck part is reduced. Moreover, since many tensile testers typically have flat chuck parts, an effect of stably fixing a specimen can be obtained, leading to better test accuracy.

Such jigs can be made, for example, by cutting based on the blueprint of the injection-molded article. For another example, such jigs can be made by filling the circumference of the injection-molded article with a cold-setting substance (e.g., silicon, epoxy) or a thermosetting substance (e.g., epoxy), removing the cured resin from the injection-molded article, and cutting the resin. For still another example, such jugs can be made by filling the circumference of the injection-molded article with a thermoplastic resin in a heat-molten state, removing the resin from the injection-molded article after cooling, and cutting the resin.

The stress-strain curve or tensile strength-strain curve can be obtained by a tensile test performed on a melt-fabricable fluororesin injection-molded article. The condition for the tensile test is not limited, and may be determined as appropriate in accordance with the subject injection-molded article. The test method of the disclosure may include a step of performing a tensile test on a melt-fabricable fluororesin injection-molded article to obtain a stress-strain curve or tensile strength-strain curve.

The stress-strain curve shows a relationship between strain generated in a tensile test and stress generated in accordance with the strain. In the stress-strain curve, commonly, strain is set to the horizontal axis (% or m; in the case of %, change rate determined by setting the initial length of the part involved in deformation or the chuck distance to 100%) and stress is set to the vertical axis (normally, MPa).

FIG. 1 is a schematic view showing an example of the stress-strain curve.

As shown in FIG. 1, the stress normally increases as the strain increases in the stress-strain curve. In the case of a defective injection-molded article due to cracks or delamination, however, the stress may decrease as the strain increases because the defective injection-molded article has a layered structure and the layers are partly fractured. The inventors found out that, in such a case, the increment of the stress relative to the strain is reduced when the stress is once lowered or even when the stress is not lowered, i.e., the gradient of the stress-strain curve becomes smaller.

Accordingly, whether or not an injection-molded article is defective due to a crack or delamination can be determined based on the stress-strain curve. Determination can be made specifically by a method described later. Still, the test method of the disclosure is not limited to the following method and those enables determination of whether or not an article is defective based on the standpoint described above is encompassed by the test method of the disclosure.

In some melt-fabricable fluororesin injection-molded articles, the stress is once reduced by a partial fracture of the layers and increases thereafter to ultimately become a large stress. In such a case, whether or not the injection-molded article is defective due to a crack or delamination cannot be determined based simply on the statistics obtained by a conventional tensile test. Even in the case of an injection-molded article having such a stress-strain curve, the novel test method of the disclosure enables determination of whether or not the article is defective.

The tensile strength-strain curve shows a relationship between strain generated in a tensile test and tensile strength generated in accordance with the strain. In the tensile strength-strain curve, normally, strain is set to the horizontal axis (% or m; in the case of %, the same applies as in the case of the stress-strain curve) and tensile strength is set to the vertical axis (normally, newton (N)).

For quality control, molded articles normally have the same size, and the stress (tensile strength per unit area) corresponds to the tensile strength at a ratio of 1:1. The quality of the molded articles can be therefore controlled based on the tensile strength, if the shape and pulling site of the molded article are limited. In other words, whether or not a melt-fabricable fluororesin injection-molded article is defective due to a crack or delamination can also be determined based on the tensile strength-strain curve in the same manner as in the case of using the stress-strain curve.

In the test method of the disclosure, determination of whether or not an article is defective is made based on the relationship between stress and strain in the case of using the stress-strain curve and based on the relationship between tensile strength and strain in the case of using the tensile strength-strain curve.

The determination criterion of the quality of the injection-molded article varies in accordance with the application thereof, and the determination criterion or method appropriate for the application may be selected. Accordingly, the same injection-molded article may be evaluated as either a defective article or a non-defective article depending on the determination criterion or the like.

In the test method of the disclosure, the stress value (absolute amount) or tensile strength value (absolute amount) of an injection-molded article is firstly measured in a tensile test. In the test method of the disclosure, whether or not the injection-molded article is defective may be determined based on the stress value (absolute amount) or tensile strength value (absolute amount) or based on the reduction rate or the like calculated from the stress value or tensile strength value.

Specifically, whether or not the injection-molded article is defective can be determined based on the reduction amount calculated from two different stress values or tensile strength values depending on the strain, or after calculating multiple reduction amounts, based on the reduction rate or reduction amount calculated from two different stress values or tensile strength values depending on the strain of the calculated multiple reduction amounts.

Alternatively, the determination may be made comprehensively based on multiple reduction amounts or reduction rates calculated from two or more different stress values or tensile strength values depending on the strain.

The condition for the tensile test is not limited, and may be appropriately set in accordance with the shape, material, or application of the injection-molded article.

The determining step preferably involves dividing the stress-strain curve or tensile strength-strain curve into two or more regions according to a strain level, obtaining a reduction amount or reduction rate of the stress or tensile strength in a large strain region relative to the stress or tensile strength in a small strain region, and determining an injection-molded article having a small reduction amount or reduction rate of the stress or tensile strength as a non-defective article and an injection-molded article having a large reduction amount or reduction rate of the stress or tensile strength as a defective article.

The number of regions is not limited, and may be 2 to 20, preferably 2 to 15, more preferably 2 to 10.

Figure 2:
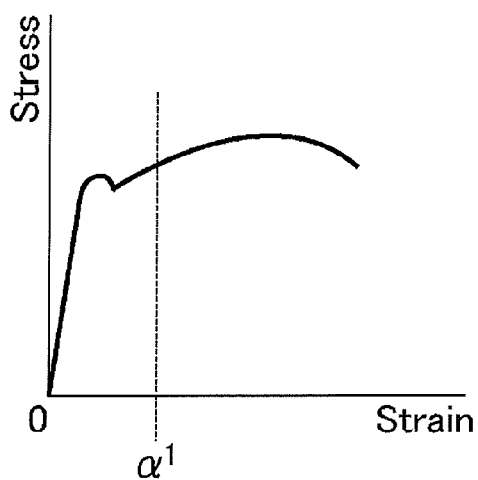
FIG. 2 is a schematic view showing an example of a stress-strain curve divided based on a strain level.
Figure 3:
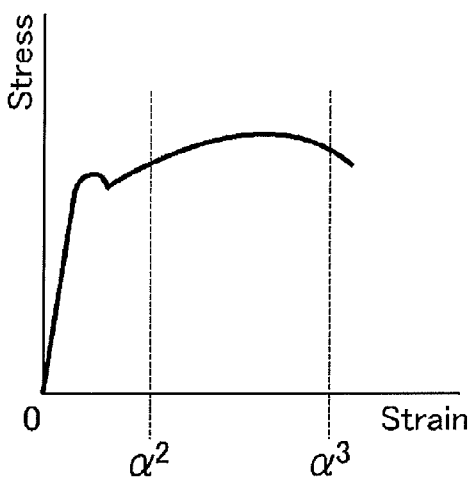
FIG. 3 is a schematic view showing an example of a stress-strain curve divided based on a strain level.
Figure 4:
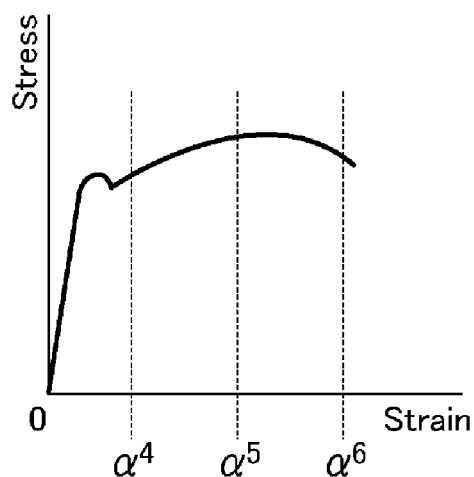
FIG. 4 is a schematic view showing an example of a stress-strain curve divided based on a strain level.

The case of dividing the curve into two or more regions according to the strain level is exemplified in, but not limited to, FIGS. 2 to 4.

In FIG. 2, the stress-strain curve is divided into two regions at a strain of a'. In FIG. 2, the small strain region is a region of the strain of a' or lower and the large strain region is a region of the strain of a' or higher. In this case, the maximum value of the strain is a strain at a fracture point at which the injection-molded article is fractured.

FIG. 3 shows a method of dividing the stress-strain curve into two regions including a region of the strain of $\alpha^2$ or lower and a region of the strain of $\alpha^2$ to $\alpha^3$. In this case, the small strain region is a region of the strain of $\alpha^2$ or lower and the large strain region is a region of the strain of $\alpha^2$ to $\alpha^3$.

FIG. 4 shows a method of dividing the stress-strain curve into a region of the strain of $\alpha^4$ or lower and a region of the strain of as to $\alpha^6$. In this case, the small strain region is a region of the strain of $\alpha^4$ or lower and the large strain region is a region of the strain of $\alpha^5$ to $\alpha^6$.

The division can be similarly made in the case of using the tensile strength-strain curve.

The "stress in a small strain region" and the "stress in a large strain region" each may be a strain randomly selected from the stress within the region or the average, integral, maximum value, or minimum value of the stress within the region.

The same applies to the case of the determination based on the tensile strength-strain curve.

Figure 8:
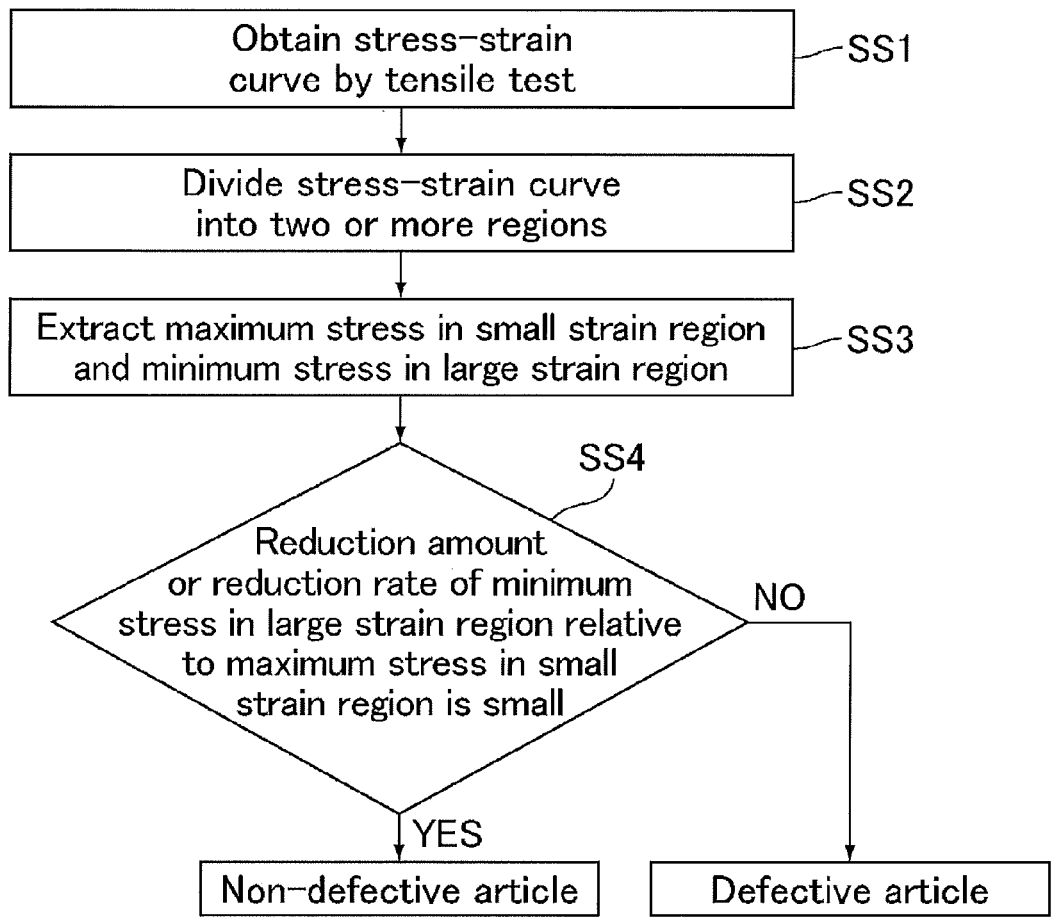
FIG. 8 is a flowchart showing an example of the test method of the disclosure.

FIG. 8 shows a flowchart showing an example of the test method. In sub-step 1 (SS1), a stress-strain curve is obtained by performing a tensile test on a melt-fabricable fluororesin injection-molded article. In SS2, the stress-strain curve is divided into two or more regions according to the strain level. In SS3, the maximum stress in the small strain region and the minimum stress in the large strain region are extracted. In SS4, finally, the reduction amount or reduction rate of the minimum stress in the large strain region relative to the maximum stress in the small strain region is calculated, and an injection-molded article having a small reduction amount or reduction rate is determined as a non-defective article and an injection-molded article having a large reduction amount or reduction rate is determined as a defective article.

The determination based on the tensile strength-strain curve can be carried out in the same manner.

According to a preferred embodiment, the determining step involves obtaining a reduction amount or reduction rate of the minimum stress or minimum tensile strength in a region of the strain of $Z^1$% to $Z^2$% (where $Z^1$ represents a value of $Y^1$ defined below to 200 and $Z^2$ represents a value of larger than $Z^1$ but not larger than 300) relative to the maximum stress or maximum tensile strength in a region of the strain of $Y^1$% or lower (where $Y^1$ represents a value of 5 to 80) in the stress-strain curve or tensile strength-strain curve, and determining an injection-molded article having a small reduction amount or reduction rate of the stress or tensile strength as a non-defective article and an injection-molded article having a large reduction amount or reduction rate of the stress or tensile strength as a defective article (hereafter, also referred to as a "determining step (1)").

The reduction amount and reduction rate of the stress can be expressed by the following equations.

Reduction amount=$SM1-Sm1$

Reduction rate=$1-(Sm1/SM1)$

In the equations, Sm1 represents the minimum stress in the region of the strain of $Z^1$% to $Z^2$% and SM1 represents the maximum stress in the region of the strain of $Y^1$% or lower.

The reduction amount and reduction rate of the tensile strength can be expressed by the following equations.

Reduction amount=$TM1-Tm1$ $$\text{Reduction rate}=1-(Tm1/TM1)$$

In the equations, Tm1 represents the minimum tensile strength in the region of the strain of $Z^1\%$ to $Z^2\%$ and TM1 represents the maximum tensile strength in the region of the strain of $Y^1\%$ or lower.

Those having a small reduction amount or reduction rate expressed by the above equations are determined as non-defective articles and those having a large reduction amount or reduction rate are determined as defective articles. In the case of Sm1>SM1 or Tm1>TM1, the value of the reduction amount or reduction rate is a negative value. In such a case, a larger negative value indicates a smaller reduction amount or reduction rate.

$Y^1$ is a value of 5 to 80, preferably 10 to 70, more preferably 15 to 60.

$Z^1$ is a value of $Y^2$ to 200, preferably 40 to 160, more preferably 50 to 150.

$Z^2$ is a value larger than $Z^2$ but not larger than 300, preferably 50 to 200, more preferably 60 to 160.

$Z^1$ is preferably a value obtained by adding at least 20 to $Y^1$, more preferably a value obtained by adding at least 25 to $Y^1$, still more preferably a value obtained by adding at least 30 to $Y^1$.

$Z^2$ is preferably a value obtained by adding at least 5 to $Z^1$, more preferably a value obtained by adding at least 10 to $Z^1$.

The determining step (1) is specifically described with reference to FIGS. 5(a) and 5(b). First, as shown in FIGS. 5(a) and 5(b), $Y^1\%$, $Z^1\%$, and $Z^2\%$ of the strain are determined, and the curve is divided into a region of the strain of $Y^1\%$ or lower and a region of the strain of $Z^1\%$ to $Z^2\%$.

Figure 5A:
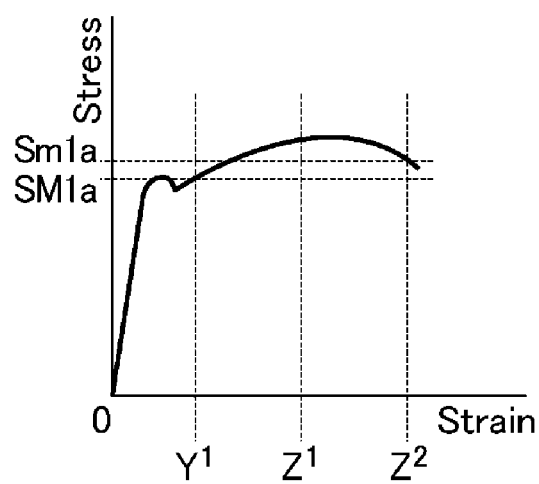
FIGS. 5(a) and 5(b) are schematic views illustrating an example of the determining step of the disclosure with use of two stress-strain curves.
Figure 5B:
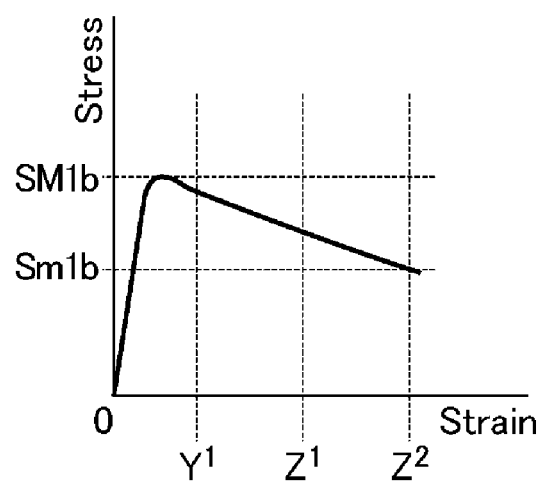

In the stress-strain curve in FIG. 5(a), the maximum stress in the region of $Y^1\%$ or lower is SM1a and the minimum stress in the region of $Z^1\%$ to $Z^2\%$ is Sm1a. The reduction amount is expressed by the following equation.

$$\text{Reduction amount}=SM1a-Sm1a$$

The reduction rate is expressed by the following equation.

$$\text{Reduction rate}=1-(Sm1a/SM1a)$$

In the stress-strain curve in FIG. 5(b), the maximum stress in the region of $Y^1\%$ or lower is SM1b and the minimum stress in the region of $Z^1\%$ to $Z^2\%$ is Sm1b. The reduction amount and the reduction rate are expressed by the following equations.

$$\text{Reduction amount}=SM1b-Sm1b$$

$$\text{Reduction rate}=1-(Sm1b/SM1b)$$

In the case of the tensile strength-strain curve, the reduction amount or reduction rate can be calculated in the same manner.

The specific criterion value of the reduction amount or reduction rate for determining whether or not the article is defective in the determining step (1) may be determined as appropriate. For example, an article having a reduction amount of 1.5 MPa or less may be determined as a non-defective article. For another example, an article having a reduction rate of 0.3 or lower may be determined as a non-defective article, and an article having a reduction rate of 0.1 or lower may be determined to have a better quality.

In the case of the tensile strength-strain curve, the criterion value may be determined as appropriate in the same manner. For example, the reduction amount of tensile strength is converted to the reduction amount of stress, and an article having a reduction amount of 1.5 MPa or less is determined as a non-defective article. As in the determination based on the stress, an article having a reduction rate of 0.3 or lower may be determined as a non-defective article, and an article having a reduction rate of 0.1 or lower may be determined to have a better quality.

According to a preferred embodiment, the determining step involves obtaining a reduction amount or reduction rate of the stress or tensile strength at a strain of $Z^3\%$ where $Z^3$ represents a value of $Y^2$ defined below to 300 relative to a maximum stress or maximum tensile strength in a region of the strain of $Y^2\%$ or lower where $Y^2$ represents a value of 5 to 80 in the stress-strain curve or tensile strength-strain curve, and determining an injection-molded article having a small reduction amount or reduction rate of the stress or tensile strength as a non-defective article and an injection-molded article having a large reduction amount or reduction rate of the stress or tensile strength as a defective article (hereafter, also referred to as a "determining step (2)").

The reduction amount and reduction rate of the stress can be expressed by the following equations.

$$\text{Reduction amount}=SM2-Sm2$$

$$\text{Reduction rate}=1-(Sm2/SM2)$$

In the equations, Sm2 represents the stress at a strain of $Z^3\%$ and SM2 represents the maximum stress in the region of the strain of $Y^2\%$ or lower.

The reduction amount and reduction rate of the tensile strength can be expressed by the following equations.

$$\text{Reduction amount}=TM2-Tm2$$

$$\text{Reduction rate}=1-(Tm2/TM2)$$

In the equations, Tm2 represents the tensile strength at a strain of $Z^3\%$ and TM2 represents the maximum tensile strength in the region of the strain of $Y^2\%$ or lower. Those having a small reduction amount or reduction rate expressed by the above equations are determined as non-defective articles and those having a large reduction amount or reduction rate are determined as defective articles. In the case of Sm2>SM2 or Tm2>TM2, the value of the reduction amount or reduction rate is a negative value. In such a case, a larger negative value indicates a smaller reduction amount or reduction rate.

$Y^2$ is a value of 5 to 80, preferably 10 to 70, more preferably 15 to 60.

$Z^3$ is a value of $Y^2$ to 300, preferably 40 to 200, more preferably 50 to 150.

$Z^3$ is preferably a value obtained by adding at least 20 to $Y^2$, more preferably a value obtained by adding at least 25 to $Y^2$, still more preferably a value obtained by adding at least 30 to $Y^2$.

Figure 6A:
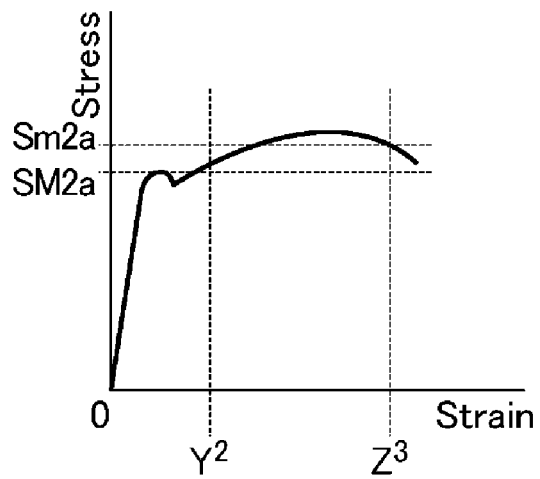
FIGS. 6(a) and 6(b) are schematic views illustrating an example of the determining step of the disclosure with use of two stress-strain curves.
Figure 6B:
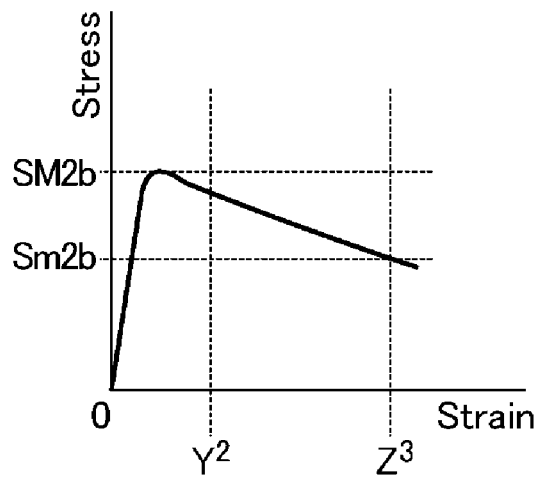

The determining step (2) is specifically described with reference to FIGS. 6(a) and 6(b). As shown in FIGS. 6(a) and 6(b), $Y^2\%$ and $Z^3\%$ of the strain are determined, and the curve is divided into a region of the strain of $Y^2\%$ or lower and a region of the strain of $Y^2\%$ or higher.

In the stress-strain curve in FIG. 6(a), the maximum stress in the region of $Y^2\%$ or lower is SM2a and the stress at $Z^3\%$ is Sm2a. The reduction amount and reduction rate are expressed by the following equations.

$$\text{Reduction amount}=SM2a-Sm2a$$

$$\text{Reduction rate}=1-(Sm2a/SM2a)$$

In the stress-strain curve in FIG. 6(b), the maximum stress in the region of $Y^2\%$ or lower is SM2b and the stress at $Z^3\%$ is Sm2b. The reduction amount and reduction rate are expressed by the following equations.

Reduction amount=$SM2b-Sm2b$

Reduction rate=$1-(Sm2b/SM2b)$

In the case of the tensile strength-strain curve, the reduction amount or reduction rate can be calculated in the same manner.

The specific criterion value of the reduction amount or reduction rate for determining whether or not the article is defective in the determining step (2) may be determined as appropriate. For example, in the case of the stress-strain curve, an article having a reduction amount of 1.5 MPa or less may be determined as a non-defective article. For another example, an article having a reduction rate of 0.3 or lower may be determined as a non-defective article, and an article having a reduction rate of 0.1 or lower may be determined to have a better quality.

In the case of the tensile strength-strain curve, the criterion value may be determined as appropriate in the same manner. For example, the reduction amount of tensile strength is converted to the reduction amount of stress, and an article having a reduction amount of 1.5 MPa or less is determined as a non-defective article. As in the determination based on the stress, an article having a reduction rate of 0.3 or lower may be determined as a non-defective article, and an article having a reduction rate of 0.1 or lower may be determined to have a better quality.

According to a preferred embodiment, the determining step involves dividing the stress-strain curve into n regions for every X % of the strain where X represents a value of 5 or larger, calculating a maximum value $SMAX_m$ and a minimum value $SMIN_m$ of the stress in each region, and determining an injection-molded article having $SMAX_m$ and $SMIN_{m+1}$ satisfying the following expression (1) as a non-defective article and an injection-molded article having $SMAX_m$ and $SMIN_{m+1}$ not satisfying the expression (1) as a defective article (hereafter, also referred to as a "determining step (3)"):

$$SMAX_m \times \alpha \le SMIN_{m+1} \quad (1)$$

where α represents a value of 0.90 or larger and m represents an integer of 1 to (n-1).

The n regions divided for every X % are numbered m=1, 2, 3 . . . in ascending order of strain. When the minimum value $SMIN_2$ of the stress in a m=2 region is larger than the value obtained by multiplying the maximum value $SMAX_1$ of the stress in a m=1 region by 0.9, the case of m=1 satisfies the expression (1).

For example, in the case of n=3, the expression (1) needs to be satisfied in the cases of m=1 and m=2. In the case of n=4, the expression (1) needs to be satisfied in the cases of m=1, m=2, and m=3.

The value of X in the expression (1) may be determined as appropriate, and may be, for example, 5 to 50, preferably 5 to 30, more preferably 10 to 20.

In the case where the stress-strain curve has a yield point, X is preferably larger than the strain at the yield point. For example, when the yield point is present at a strain of 5%, X is preferably a value larger than 5.

The value of n in the expression (1) may be determined as appropriate. The value of X×n (%) only needs to be smaller than the strain (%) at the fracture point in the stress-strain curve. Larger n enables determination at a more detailed level.

The value of α in the expression (1) only needs to be 0.90 or larger and may be determined as appropriate. The value of a is preferably 0.92 or larger, more preferably 0.95 or larger. The maximum value of a may be 1.00.

Figure 7A:
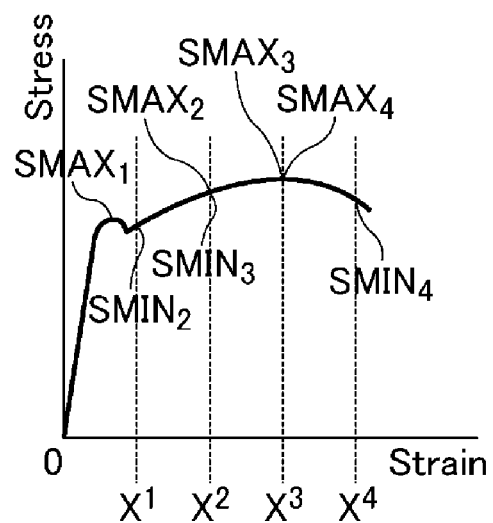
FIGS. 7(a) and 7(b) are schematic views illustrating an example of the determining step of the disclosure with use of two stress-strain curves.
Figure 7B:
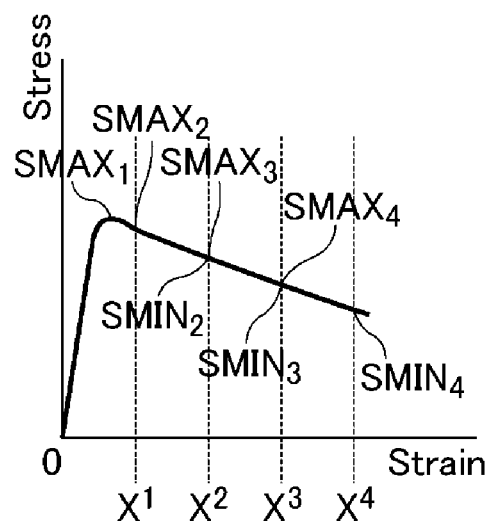

The determining step (3) is specifically described with reference to FIGS. 7(a) and 7(b). As shown in FIGS. 7(a) and 7(b), when the strain axis is divided for every X % (in FIGS. 7(a) and 7(b), $X^1$=X, $X^2$=2X, $X^3$=3X, and $X^4$=4X), a strain range of 0 to $X^1$ is a m=1 region, a strain range of $X^1$ to $X^2$ is a m=2 region, a strain range of $X^2$ to $X^3$ is a m=3 region, and a strain range of $X^3$ to $X^4$ is a m=4 region. The minimum stress $SMIN_2$ in the m=2 region needs to be larger than the value obtained by multiplying the maximum stress $SMAX_1$ in the m=1 region by 0.9. An article satisfying the expression (1) also in the m=2 to 4 regions is determined as a non-defective article. An article not satisfying the expression (1) in any one of the regions is determined as a defective article.

In the case of the stress-strain curve in FIG. 7(a), the expression (1) is satisfied in all the m=1 to 4 regions. Accordingly, the injection-molded article is determined as a non-defective article. In the case of the stress-strain curve in FIG. 7(b), the expression (1) is not satisfied in any of the m=1 to 4 regions. Accordingly, the injection-molded article is determined as a defective article.

According to a preferred embodiment, the determining step involves dividing the tensile strength-strain curve into n regions for every X % of the strain where X represents a value of 5 or larger, calculating a maximum value $TMAX_m$ and a minimum value $TMIN_m$ of the tensile strength in each region, and determining an injection-molded article having $TMAX_m$ and $TMIN_{m+1}$ satisfying the following expression (2) as a non-defective article and an injection-molded article having $TMAX_m$ and $TMIN_{m+1}$ not satisfying the expression (2) as a defective article (hereafter, also referred to as a "determining step (4)"):

$$TMAX_m \times \alpha \le TMIN_{m+1} \quad (2)$$

where α represents a value of 0.90 or larger and m represents an integer of 1 to (n-1).

The n regions divided for every X % are numbered m=1, 2, 3 . . . in ascending order of strain. When the minimum value $TMIN_2$ of the tensile strength in a m=2 region is larger than the value obtained by multiplying the maximum value $TMAX_1$ of the tensile strength in a m=1 region by 0.9, the case of m=1 satisfies the expression (2).

For example, in the case of n=3, the expression (2) needs to be satisfied in the cases of m=1 and m=2. In the case of n=4, the expression (2) needs to be satisfied in the cases of m=1, m=2, and m=3.

The value of X in the expression (2) may be determined as appropriate, and may be, for example, 5 to 50, preferably 5 to 30, more preferably 10 to 20.

In the case where the tensile strength-strain curve has a yield point, X is preferably larger than the strain at the yield point. For example, when the yield point is present at a strain of 5%, X is preferably a value larger than 5.

The value of n in the expression (2) may be determined as appropriate. The value of X×n (%) only needs to be smaller than the strain (%) at the fracture point in the tensile strength-strain curve. Larger n enables determination at a more detailed level.

The value of α in the expression (2) only needs to be 0.90 or larger and may be determined as appropriate. The value of α is preferably 0.92 or larger, more preferably 0.95 or larger. The maximum value of α may be 1.00.

The test method of the disclosure enables easy determination of whether or not a melt-fabricable fluororesin injection-molded article is defective, and therefore is useful for adjustment of the molding condition for injection molding of a melt-fabricable fluororesin. The test method of the disclosure is also employable for sorting non-defective articles from defective articles in production of injection-molded articles, acceptance inspection of molded articles, and the like.

The method for producing a melt-fabricable fluororesin injection-molded article of the disclosure includes: (x) injection-molding a melt-fabricable fluororesin of a lot to obtain multiple injection-molded articles; (y) randomly selecting one injection-molded article from the multiple injection-molded articles and determining whether or not the selected injection-molded article is defective due to a crack or delamination based on a stress-strain curve obtained by a tensile test; and (z) sorting out a non-defective article in the injection-molded articles produced from the melt-fabricable fluororesin of the same lot from which the injection-molded article determined as a defective article has been produced.

The production method of the disclosure enables easy determination of whether or not a melt-fabricable fluororesin injection-molded article is defective due to a crack or delamination, improving the productivity.

The step (x) involves injection-molding a melt-fabricable fluororesin of a lot to obtain multiple injection-molded articles. The injection-molded articles obtained from the melt-fabricable fluororesin of the same lot highly possibly have similar properties. It is reasonable that the step (y) described later is carried out for each lot of the melt-fabricable fluororesin.

The step (y) involves randomly selecting at least one injection-molded article from the multiple injection-molded articles. The number of selected injection-molded articles may be one or two or more.

The determination of whether or not the injection-molded article is defective due to a crack or delamination based on the stress-strain curve or tensile strength-strain curve obtained by a tensile test can be carried out in the same manner as in the determining step in the test method of the disclosure described above.

The step (z) involves sorting out a non-defective article in the injection-molded articles produced from the melt-fabricable fluororesin of the same lot from which the injection-molded article determined as a defective article has been produced. The sorting method is not limited. In the case where a non-defective article cannot be sorted out nondestructively from the injection-molded articles obtained from the melt-fabricable fluororesin of the same lot, all the injection-molded articles obtained from the melt-fabricable fluororesin of the same lot may be eliminated.

The production method of the disclosure can produce a melt-fabricable fluororesin injection-molded article while eliminating a defective article due to a crack or delamination.

EXAMPLES

The test method and the production method of the disclosure are described in the following with reference to, but not limited to, examples.

In the examples, the following melt-fabricable fluororesin was used.

Melt-fabricable fluororesin 1: TFE/PPVE copolymer, TFE/PPVE=98.5/1.5 (molar ratio), MFR: 15.2 g/10 min The melt flow rate (MFR) of the melt-fabricable fluororesin used in the examples was measured in accordance with ASTM D 1238 at a temperature of 372° C. and a load of 5 kg.

Production Example 1

Four injection-molded articles (30 mm×60 mm, 1.0 mm in thickness) were obtained from the melt-fabricable fluororesin 1 using an injection molding machine MDX75XA (produced by Ube Machinery Corporation Ltd.) under the conditions of an injection speed of 50 mm/s, a header temperature of 375° C., and a mold temperature of 180° C.

Production Example 2

Four injection-molded articles were obtained as in Production Example 1, except that the injection speed was changed to 40 mm/s.

Production Example 3

Four injection-molded articles were obtained as in Production Example 1, except that the injection speed was changed to 30 mm/s.

Production Example 4

Four injection-molded articles were obtained as in Production Example 1, except that the injection speed was changed to 20 mm/s.

Production Example 5

Four injection-molded articles were obtained as in Production Example 4, except that the header temperature was changed to 370° C.

Production Example 6

Four injection-molded articles were obtained as in Production Example 1, except that the injection speed was changed to 10 mm/s.

Tensile Test

The injection-molded articles obtained in Production Example 1 were subjected to a tensile test under the following conditions, whereby stress-strain curves were obtained.

The injection-molded articles obtained in Production Example 4 were subjected to a tensile test under the following conditions, whereby stress-strain curves were obtained.

[Condition for Tensile Test]

Figure 9:
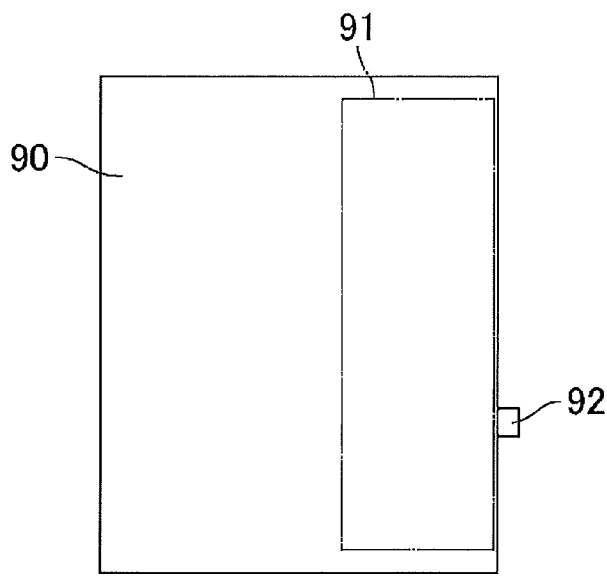
FIG. 9 is a schematic view showing a region of an injection-molded article from which a specimen is cut out in examples.

A specimen in the shape in accordance with ASTM D1708 was subjected to the measurement at a tensile speed of 50 mm/sec at room temperature. FIG. 9 is a schematic view showing a region of an injection-molded article from which a specimen is cut out. The specimen was produced by cutting out a region 91 surrounded by a dash-dot line from an injection-molded article 90 shown in FIG. 9. A gate portion is indicated by 92 in FIG. 9.

Example 1-1

The stress-strain curve was divided into a region A1 of the strain of 20% or lower and a region B1 of the strain of 50% to 60%. The maximum stress in the region A1 and the minimum stress in the region B1 were extracted.

In some cases of the four injection-molded articles obtained in Production Example 1, the reduction rate of the minimum stress relative to the maximum stress was higher than 10%. Those having a reduction rate of higher than 10% were determined as defective articles due to a crack or delamination.

In any case of the four injection-molded articles obtained in Production Example 2, the reduction rate of the minimum stress relative to the maximum stress was 0% or lower. Accordingly, all the injection-molded articles were determined as non-defective articles.

Example 1-2

The stress-strain curve was divided into a region A2 of the strain of 20% or lower and a region B2 of the strain of 60% to 70%. The maximum stress in the region A2 and the minimum stress in the region B2 were extracted.

In some cases of the four injection-molded articles obtained in Production Example 1, the reduction rate of the minimum stress relative to the maximum stress was higher than 10%. Those having a reduction rate of higher than 10% were determined as defective articles due to a crack or delamination.

In any case of the four injection-molded articles obtained in Production Example 4, the reduction rate of the minimum stress relative to the maximum stress was 0% or lower. Accordingly, all the injection-molded articles were determined as non-defective articles.

Example 1-3

The stress-strain curve was divided into a region A3 of the strain of 20% or lower and a region B3 of the strain of 100% to 110%. The maximum stress in the region A3 and the minimum stress in the region B3 were extracted.

In some cases of the four injection-molded articles obtained in Production Example 1, the reduction rate of the minimum stress relative to the maximum stress was higher than 10%. Those having a reduction rate of higher than 10% were determined as defective articles due to a crack or delamination.

In any case of the four injection-molded articles obtained in Production Example 4, the reduction rate of the minimum stress relative to the maximum stress was higher than 10%. Accordingly, all the injection-molded articles were determined as defective articles.

Example 1-4

The stress-strain curve was divided into a region A4 of the strain of 20% or lower and a region B4 of the strain of 150% to 160%. The maximum stress in the region A4 and the minimum stress in the region B4 were extracted.

In some cases of the four injection-molded articles obtained in Production Example 1, the reduction rate of the minimum stress relative to the maximum stress was higher than 10%. Those having a reduction rate of higher than 10% were determined as defective articles due to a crack or delamination.

In any case of the four injection-molded articles obtained in Production Example 4, the reduction rate of the minimum stress relative to the maximum stress was higher than 10%. Accordingly, all the injection-molded articles were determined as defective articles.

Example 1-5

The stress-strain curve was divided into a region A5 of the strain of 60% or lower and a region B5 of the strain of 50% to 60%. The maximum stress in the region A5 and the minimum stress in the region B5 were extracted.

In some cases of the four injection-molded articles obtained in Production Example 1, the reduction rate of the minimum stress relative to the maximum stress was higher than 10%. Those having a reduction rate of higher than 10% were determined as defective articles due to a crack or delamination.

In any case of the four injection-molded articles obtained in Production Example 4, the measured value of a reduction rate of the minimum stress relative to the maximum stress was lower than 9%. Accordingly, all the injection-molded articles were determined as non-defective articles.

Example 1-6

The stress-strain curve was divided into a region A6 of the strain of 60% or lower and a region B6 of the strain of 60% to 70%. The maximum stress in the region A6 and the minimum stress in the region B6 were extracted.

In some cases of the four injection-molded articles obtained in Production Example 1, the reduction rate of the minimum stress relative to the maximum stress was higher than 10%. Those having a reduction rate of higher than 10% were determined as defective articles due to a crack or delamination.

In any case of the four injection-molded articles obtained in Production Example 4, the measured value of a reduction rate of the minimum stress relative to the maximum stress was lower than 9%. Accordingly, all the injection-molded articles were determined as non-defective articles.

Example 1-7

The stress-strain curve was divided into a region A7 of the strain of 60% or lower and a region B7 of the strain of 100% to 110%. The maximum stress in the region A7 and the minimum stress in the region B7 were extracted.

In some cases of the four injection-molded articles obtained in Production Example 1, the reduction rate of the minimum stress relative to the maximum stress was higher than 10%. Those having a reduction rate of higher than 10% were determined as defective articles due to a crack or delamination.

In any case of the four injection-molded articles obtained in Production Example 4, the reduction rate of the minimum stress relative to the maximum stress was higher than 10%. Accordingly, all the injection-molded articles were determined as defective articles.

Example 1-8

The stress-strain curve was divided into a region A8 of the strain of 60% or lower and a region B8 of the strain of 150% to 160%. The maximum stress in the region A8 and the minimum stress in the region B8 were extracted.

In some cases of the four injection-molded articles obtained in Production Example 1, the reduction rate of the minimum stress relative to the maximum stress was higher than 10%. Those having a reduction rate of higher than 10% were determined as defective articles due to a crack or delamination.

In any case of the four injection-molded articles obtained in Production Example 4, the reduction rate of the minimum stress relative to the maximum stress was higher than 10%. Accordingly, all the injection-molded articles were determined as defective articles.

Example 2-1

The stress-strain curve was divided into a region C1 of the strain of 20% or lower and a region D1 of the strain of 20% or higher. The maximum stress in the region C1 was extracted. The stress at a strain of 50% in the region D1 was extracted.

In any case of the four injection-molded articles obtained in Production Example 1, the stress at a strain of 50% relative to the maximum stress was lower than 9%. Accordingly, all the injection-molded articles were determined as non-defective articles without a crack or delamination.

In any case of the four injection-molded articles obtained in Production Example 4, the measured value of the reduction rate of the stress at a strain of 50% relative to the maximum stress was lower than 9%. Accordingly, all the injection-molded articles were determined as non-defective articles.

Example 2-2

The stress-strain curve was divided into a region C2 of the strain of 20% or lower and a region D2 of the strain of 20% or higher. The maximum stress in the region C2 was extracted. The stress at a strain of 60% in the region D2 was extracted.

In some cases of the four injection-molded articles obtained in Production Example 1, the reduction rate of the stress at a strain of 60% relative to the maximum stress was higher than 10%. Those having a reduction rate of higher than 10% were determined as defective articles due to a crack or delamination.

In any case of the four injection-molded articles obtained in Production Example 4, the reduction rate of the stress at a strain of 60% relative to the maximum stress was lower than 9%. Accordingly, all the injection-molded articles were determined as non-defective articles.

Example 2-3

The stress-strain curve was divided into a region C3 of the strain of 20% or lower and a region D3 of the strain of 20% or higher. The maximum stress in the region C3 was extracted. The stress at a strain of 100% in the region D3 was extracted.

In any case of the four injection-molded articles obtained in Production Example 1, the reduction rate of the stress at a strain of 100% relative to the maximum stress was higher than 10%. Accordingly, all the injection-molded articles were determined as defective articles due to a crack or delamination.

In some cases of the four injection-molded articles obtained in Production Example 4, the reduction rate of the stress at a strain of 100% relative to the maximum stress was higher than 9%. Those having a reduction rate of higher than 9% were determined as defective articles.

Example 2-4

The stress-strain curve was divided into a region C4 of the strain of 20% or lower and a region D4 of the strain of 20% or higher. The maximum stress in the region C4 was extracted. The stress at a strain of 150% in the region D4 was extracted.

In any case of the four injection-molded articles obtained in Production Example 1, the reduction rate of the stress at a strain of 150% relative to the maximum stress was higher than 10%. Accordingly, all the injection-molded articles were determined as defective articles due to a crack or delamination.

In some cases of the four injection-molded articles obtained in Production Example 4, the reduction rate of the stress at a strain of 150% relative to the maximum stress was higher than 9%. Those having a reduction rate of higher than 9% were determined as defective articles.

Example 2-5

The stress-strain curve was divided into a region C5 of the strain of 60% or lower and a region D5 of the strain of 60% or higher. The maximum stress in the region C5 was extracted. The stress at a strain of 60% in the region D5 was extracted.

In any case of the four injection-molded articles obtained in Production Example 1, the reduction rate of the stress at a strain of 60% relative to the maximum stress was higher than 10%. Accordingly, all the injection-molded articles were determined as defective articles due to a crack or delamination.

In any case of the four injection-molded articles obtained in Production Example 4, the reduction rate of the stress at a strain of 60% relative to the maximum stress was lower than 9%. Accordingly, all the injection-molded articles were determined as non-defective articles.

Example 2-6

The stress-strain curve was divided into a region C6 of the strain of 60% or lower and a region D6 of the strain of 60% or higher. The maximum stress in the region C6 was extracted. The stress at a strain of 100% in the region D6 was extracted.

In any case of the four injection-molded articles obtained in Production Example 1, the reduction rate of the stress at a strain of 100% relative to the maximum stress was higher than 10%. Accordingly, all the injection-molded articles were determined as defective articles due to a crack or delamination.

Example 2-7

The stress-strain curve was divided into a region C7 of the strain of 60% or lower and a region D7 of the strain of 60% or higher. The maximum stress in the region C7 was extracted. The stress at a strain of 150% in the region D7 was extracted.

In any case of the four injection-molded articles obtained in Production Example 1, the reduction rate of the stress at a strain of 150% relative to the maximum stress was higher than 10%. Accordingly, all the injection-molded articles were determined as defective articles due to a crack or delamination.

In any case of the four injection-molded articles obtained in Production Example 4, the reduction rate of the stress at a strain of 150% relative to the maximum stress was higher than 9%. Accordingly, all the injection-molded articles were determined as defective articles.

Example 3-1

Four molded articles obtained in each of Production Examples 1 to 6 were subjected to a tensile test, whereby stress-strain curves were obtained. The stress-strain curves were each divided into 10 regions for every 10% of the strain. The regions were numbered m=1 to 9 in ascending order of strain.

The maximum stress and minimum stress in each region were extracted, and whether or not they satisfy the following expression was determined:

$$SMAX_m \times \alpha \leq SMIN_{m+1}$$

($\alpha=0.93$, m=integer of 1 to 9).

Table 1 below shows $SMIN_{m+1}/SMAX_m$ in the cases of m=1 to 9 for each production example. In Table 1, the case where a is 0.92 or less is shown by a box colored gray.

In Table 1, the column of m=1 shows the values of $(1-SMIN_2/SMAX_1)\times 100$ and the column of m=2 shows the values of $(1-SMIN_3/SMAX_2)\times 100$.

Two injection molded articles out of four articles obtained in Production Example 1 satisfied the above expression in the regions of m=1 to 4 but failed to satisfy the above expression when m reached 5. Accordingly, the two injection-molded articles were determined as defective articles. The other two injection-molded articles satisfied the above expression in the regions of m=1 to 5 but failed to satisfy the above expression when m reached 6. Accordingly, these two injection-molded articles were determined as defective articles.

One injection-molded articles out of four articles obtained in Production Example 2 failed to satisfy the above expression when m reached 5, and therefore was determined as a defective article. Another one injection-molded article satisfied the above expression in the regions of m=1 to 5 but failed to satisfy the above expression when m reached 6. Accordingly, the injection-molded article was determined as a defective article. Another one injection-molded article satisfied the above expression in the regions of m=1 to 7 but failed to satisfy the above expression when m reached 8. Accordingly, the injection-molded article was determined as a defective article. The last one injection-molded article satisfied the above expression in the regions of m=1 to 9, and therefore was determined as a non-defective article.

One injection-molded article out of four articles obtained in Production Example 3 failed to satisfy the above expression when m reached 6, and therefore was determined as a defective article. Another one injection-molded article satisfied the above expression in the regions of m=1 to 5 but failed to satisfy the above expression when m reached 6. Accordingly, the injection-molded article was determined as a defective article. Another one injection-molded article satisfied the above expression in the regions of m=1 to 6 but failed to satisfy the above expression when m reached 7. Accordingly, the injection-molded article was determined as a defective article. The remaining two injection-molded articles satisfied the above expression in the regions of m=1 to 8, and therefore was determined as non-defective articles.

Four injection-molded articles obtained in Production Example 4 all satisfied the above expression until m reached 8, and therefore were determined as non-defective articles.

One injection-molded article out of four articles obtained in Production Example 5 failed to satisfy the above expression when m reached 6, and therefore was determined as a defective article. The other three injection-molded articles failed to satisfy the above expression when m reached 7, and therefore were determined as defective articles.

Three injection-molded articles out of four articles obtained in Production Example 6 already failed to satisfy the above expression when m=1, and therefore were determined as defective articles. The last one injection-molded article obtained in Production Example 6 satisfied the above expression until m reached 9, and therefore was determined as a non-defective article.

Based on the above results, the value of m of the region in which the above expression was first not satisfied was used as a score, which can be used as an index of the degree to which the number of defects is small. The scores of the injection-molded articles obtained in Production Examples 1 to 6 are listed below.

Production Example 1: 5 (satisfying the above expression in the regions of m=1 to 4)
Production Example 2: 5 (satisfying the above expression in the regions of m=1 to 4)
Production Example 3: 6 (satisfying the above expression in the regions of m=1 to 5)
Production Example 4: 9 (satisfying the above expression in the regions of m=1 to 8)
Production Example 5: 6 (satisfying the above expression in the regions of m=1 to 5)
Production Example 6: 1 (not satisfying the above expression even in the region of m=1)

TABLE 1

| | $SMAX_1$ (MPa) | m = 1 | m = 2 | m = 3 | m = 4 | m = 5 | m = 6 | m = 7 | m = 8 | m = 9 |
|---|---|---|---|---|---|---|---|---|---|---|
| Production Example 1 | 13.3 | 0% | 0% | 0% | 1% | 16% | 26% | 23% | 11% | 0% |
| Injection speed | 13.1 | 0% | 1% | 0% | 1% | 12% | 15% | 6% | 3% | 0% |
| 50 mm/s | 13.1 | 1% | 1% | 0% | 0% | 7% | 12% | 15% | 18% | 5% |
| | 13.4 | 0% | 1% | 0% | 0% | 5% | 12% | 18% | 20% | 8% |
| Production Example 2 | 13.9 | 0% | 0% | 0% | 0% | 4% | 9% | 14% | 20% | 17% |
| Injection speed | 14.2 | 0% | 0% | 0% | 0% | 0% | 0% | 2% | 4% | 6% |
| 40 mm/s | 13.0 | 0% | 0% | 0% | 0% | 3% | 4% | 4% | 19% | 24% |
| | 14.2 | 0% | 0% | 0% | 2% | 14% | 20% | 20% | 13% | 0% |
| Production Example 3 | 13.5 | 0% | 0% | 0% | 0% | 0% | 0% | 23% | 23% | 0% |
| Injection speed | 13.6 | 0% | 0% | 0% | 0% | 0% | 0% | 1% | 3% | 16% |
| 30 mm/s | 13.3 | 0% | 0% | 0% | 0% | 0% | 0% | 0% | 0% | 0% |
| | 13.1 | 0% | 0% | 0% | 0% | 0% | 10% | 9% | 2% | 5% |
| Production Esample 4 | 13.2 | 0% | 0% | 0% | 0% | 1% | 1% | 0% | 0% | 18% |
| injection speed | 13.3 | 1% | 1% | 0% | 0% | 0% | 0% | 0% | 0% | 0% |
| 20 mm/s | 12.9 | 1% | 0% | 0% | 0% | 0% | 0% | 0% | 0% | 0% |
| | 13.0 | 1% | 0% | 0% | 0% | 0% | 0% | 0% | 2% | 14% |
| Producton Example 5 | 13.8 | 6% | 4% | 1% | 2% | 2% | 2% | 7% | 14% | 9% |
| Injection speed | 13.7 | 6% | 5% | 1% | 0% | 0% | 1% | 1% | 15% | 14% |
| 20 mm/s | 13.6 | 8% | 8% | 1% | 0% | 2% | 4% | 7% | 14% | 21% |
| | 13.6 | 7% | 6% | 2% | 2% | 2% | 16% | 16% | 4% | 19% |
| Production Example 6 | 13.3 | 9% | 8% | 4% | 2% | 0% | 5% | 7% | 1% | 0% |
| Injection speed | 13.3 | 10% | 8% | 3% | 1% | 0% | 0% | 1% | 1% | 0% |

TABLE 1-continued

| | SMAX₁ (MPa) | m = 1 | m = 2 | m = 3 | m = 4 | m = 5 | m = 6 | m = 7 | m = 8 | m = 9 |
|---|---|---|---|---|---|---|---|---|---|---|
| 10 mm/s | 13.2 | 6% | 4% | 2% | 1% | 0% | 0% | 0% | 0% | 0% |
| | 13.6 | 10% | 8% | 3% | 1% | 0% | 0% | 0% | 0% | 0% |

REFERENCE SIGNS LIST

90: injection-molded article
91: region from which specimen is cut out
92: gate portion

The invention claimed is:

1. A method for testing a melt-fabricable fluororesin injection-molded article, the method comprising
performing a tensile test on the injection-molded article to obtain a stress-strain curve or tensile strength-strain curve,
dividing the stress-strain curve or tensile strength-strain curve into two or more regions according to a strain level, obtaining a reduction amount or reduction rate of the stress or tensile strength in a large strain region relative to the stress or tensile strength in a small strain region,
determining an injection-molded article having a small reduction amount or reduction rate of the stress or tensile strength as a non-defective article due to a crack or delamination and an injection-molded article having a large reduction amount or reduction rate of the stress or tensile strength as a defective article due to a crack or delamination, and
sorting out non-defective articles from defective articles among the injection-molded articles.

2. The test method according to claim 1,
wherein the determining further involves obtaining a reduction amount or reduction rate of a minimum stress or minimum tensile strength in a region of the strain of $Z^1\%$ to $Z^2\%$, where $Z^1$ represents a value of $Y^1$ defined below to 200 and $Z^2$ represents a value of larger than $Z^1$ but not larger than 300, relative to a maximum stress or maximum tensile strength in a region of the strain of $Y^1\%$ or lower, where $Y^1$ represents a value of 5 to 80, in the stress-strain curve or tensile strength-strain curve, and
determining an injection-molded article having a small reduction amount or reduction rate of the stress or tensile strength as a non-defective article and an injection-molded article having a large reduction amount or reduction rate of the stress or tensile strength as a defective article.

3. The test method according to claim 1,
wherein the determining further involves obtaining a reduction amount or reduction rate of the stress or tensile strength in a region of the strain of $Z^3\%$, where $Z^3$ represents a value of $Y^2$ defined below to 300, relative to a maximum stress or maximum tensile strength in a region of the strain of $Y^2\%$ or lower, where $Y^2$ represents a value of 5 to 80, in the stress-strain curve or tensile strength-strain curve, and
determining an injection-molded article having a small reduction amount or reduction rate of the stress or tensile strength as a non-defective article and an injection-molded article having a large reduction amount or reduction rate of the stress or tensile strength as a defective article.

4. The test method according to claim 1,
wherein the determining further involves dividing the stress-strain curve into n regions for every X % of the strain where X represents a value of 5 or larger, calculating a maximum value $SMAX_m$ and a minimum value $SMIN_m$ of the stress in each region, and
determining an injection-molded article having $SMAX_m$ and $SMIN_{m+1}$ satisfying the following expression (1) as a non-defective article and an injection-molded article having $SMAX_m$ and $SMIN_{m+1}$ not satisfying the expression (1) as a defective article:

$$SMAX_m \times \alpha \leq SMIN_{m+1} \tag{1}$$

where $\alpha$ represents a value of 0.90 or larger and m represents an integer of 1 to (n−1).

5. The test method according to claim 1,
wherein the determining further involves dividing the tensile strength-strain curve into n regions for every X % of the strain where X represents a value of 5 or larger, calculating a maximum value $TMAX_m$ and a minimum value $TMIN_m$ of the tensile strength in each region, and
determining an injection-molded article having $TMAX_m$ and $TMIN_{m+1}$ satisfying the following expression (2) as a non-defective article and an injection-molded article having $TMAX_m$ and $TMIN_{m+1}$ not satisfying the expression (2) as a defective article:

$$TMAX_m \times \alpha \leq TMIN_{m+1} \tag{2}$$

where $\alpha$ represents a value of 0.90 or larger and m represents an integer of 1 to (n−1).

6. The test method according to claim 1,
wherein the melt-fabricable fluororesin injection-molded article comprises a fluororesin comprising at least one selected from the group consisting of a
tetrafluoroethylene/perfluoro(alkyl vinyl ether) copolymer and a
tetrafluoroethylene/hexafluoropropylene copolymer.

7. A method for testing melt-fabricable fluororesin injection-molded articles, the method comprising
providing a lot of melt-fabricable fluororesin injection-molded articles;
randomly selecting at least one injection-molded article from the lot of injection-molded articles;
performing a tensile test on the injection-molded article to obtain a stress-strain curve or tensile strength-strain curve,
dividing the stress-strain curve or tensile strength-strain curve into two or more regions according to a strain level, obtaining a reduction amount or reduction rate of the stress or tensile strength in a large strain region relative to the stress or tensile strength in a small strain region,
determining an injection-molded article having a small reduction amount or reduction rate of the stress or tensile strength as a non-defective article due to a crack or delamination and an injection-molded article having a large reduction amount or reduction rate of the stress or tensile strength as a defective article due to a crack or delamination; and sorting out non-defective melt-fabricable fluororesin injection-molded articles from defective articles among the injection-molded articles.

* * * * *